United States Patent [19]

Garcia

[11] 4,142,527

[45] Mar. 6, 1979

[54] ENDOTRACHEAL TUBE HOLDER

[76] Inventor: Nelson C. Garcia, P.O. Box 3804, Quito, Ecuador

[21] Appl. No.: 766,558

[22] Filed: Feb. 7, 1977

[51] Int. Cl.² .......................................... A61M 25/02
[52] U.S. Cl. ............................ 128/348; 128/DIG. 26
[58] Field of Search .............................. 128/348–351, 128/206, 208, 133, DIG. 26

[56] References Cited

U.S. PATENT DOCUMENTS

| | | | |
|---|---|---|---|
| 3,288,136 | 11/1966 | Lund | 128/133 |
| 3,399,668 | 9/1968 | Lundgren | 128/348 |
| 3,508,554 | 4/1970 | Sheridan | 128/348 |
| 3,677,250 | 2/1971 | Thomas | 128/348 |
| 3,878,849 | 4/1975 | Muller et al. | 128/349 R |
| 3,924,636 | 12/1975 | Addison | 128/351 |
| 3,972,321 | 8/1976 | Proctor | 128/348 |
| 3,977,407 | 8/1976 | Coleman et al. | 128/348 |

Primary Examiner—Dalton L. Truluck
Attorney, Agent, or Firm—Finnegan, Henderson, Farabow & Garrett

[57] ABSTRACT

An endotracheal tube holder for securing an endotracheal tube in a selected position in a patient's trachea. A support strip having an adhesive-backed material to secure the support strip to the patient's face is configured to be positioned in the naso-lip area of the patient's face between the lower portion of the nose and the upper lip and to spread from cheek to cheek. A locking strip comprising a "Velcro" material portion, and a pad comprising a material which interlocks with "Velcro" material are attached to the support strip. The endotracheal tube having a presealed ring at a selected location comprising a material which interlocks with "Velcro" material is used, such that the locking strip can be locked around the presealed ring and to the pad to lock the tube in the selected position and prevent its rotation.

3 Claims, 5 Drawing Figures

ENDOTRACHEAL TUBE HOLDER

BACKGROUND OF THE INVENTION

1. Field of the Invention

The invention relates to the medical field and particularly to an endotracheal tube holder.

2. Description of the Prior Art

The use of endotracheal tubes for insertion into the patient's trachea during surgery is general practice. The prior art discloses holding devices for fixing the position of the tube.

For example, the Addison U.S. Pat. No. 3,924,636 discloses a holder for an endotracheal tube which includes a flexible adhesive-backed strip adapted to be secured around the mouth of the patient. The strip is provided with a central opening through which the tube can be inserted. A holding strap which may include "Velcro" material is mounted on the strip adjacent to the opening, and when the endotracheal tube is properly positioned, the holding strap is wrapped around the tube and fastened to hold the tube in place.

Lund U.S. Pat. No. 3,288,136 relates to a device for mounting a flexible cylindrical object or tube to a patient, wherein a pad having an adhesive coating is applied to the patient. The tube is held in place by a "Velcro" material. The Boyd U.S. Pat. No. 3,834,380 also relates to a holder for tubular items having a strip of adhesively-backed tape which is attached to the patient. A locking means is provided with interlocking "Velcro" parts.

SUMMARY OF THE INVENTION

This invention provides distinct advantages over prior-art endotracheal tube holders. In accordance with the invention, the holder is used in conjunction with an endotracheal tube which includes a presealed ring of predetermined length that is marked according to normative charts to determine the length of insertion of the tube in the patient. The ring comprises a cloth or other type of soft fluffy material to obviate the possibility of lacerations should it come into contact with the patient's lips or bucal mucosa.

The tube holder comprises an adhesive backed support strip of soft flexible material which is attached to the patient's face. This strip is configured to be centered between the bottom portion of the nose and the upper lip, and to spread lengthwise from cheek to cheek. A locking strip comprising a "Velcro" material portion is attached to the adhesive backed strip. When the endotracheal tube is inserted into the patient's mouth the desired distance, the "Velcro" portion of the locking strip is locked around the ring, and to a fluffy material portion attached to the support strip. This securely locks the tube in the desired position.

The locking of the "Velcro" locking strip to the fluffy material portion attached to the support strip serves to prevent slippage of the tube during prolonged intubations, where tension between the material of the presealed ring and the "Velcro" portion of the locking strip might tend to wear off. The lock between the "Velcro" portion and the ring prevents rotary movement of the tube, which could otherwise cause discomfort to the patient.

The invention thus provides a more solid fixation of the tube relative to prior art devices, and prevents accidental slippage and rotation of the tube. Further, rapid adjustment of the depth of insertion of the tube is provided by varying the locking position or selecting tubes having differently located presealed rings. The ease of accessibility of the holder enables adjustment of the position of the tube, if required, without causing additional skin trauma to the patient, while reducing the time and inherent cost of a specialist in positioning the tube.

DETAILED DESCRIPTION OF THE INVENTION

Figure 1:
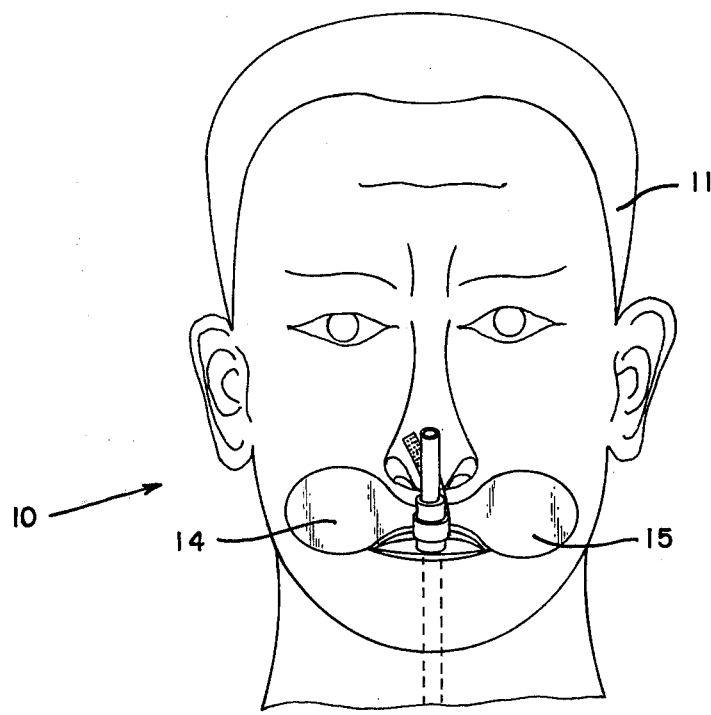
FIG. 1 is an isometric frontal view of a patient with the endotracheal tube holder of the invention in position.

FIG. 1 shows the application of the endotracheal tube holder 10 in accordance with the invention to a patient 11. The tube holder comprises a flexible adhesive-backed support strip 12 for securing it to the patient's face from cheek to cheek. The strip is centered between the lower portion of the nose and the upper lip and spreads from cheek to cheek, and defines an indented portion 13 to accommodate the relatively narrow distance in the naso-lip area.

Figure 2:
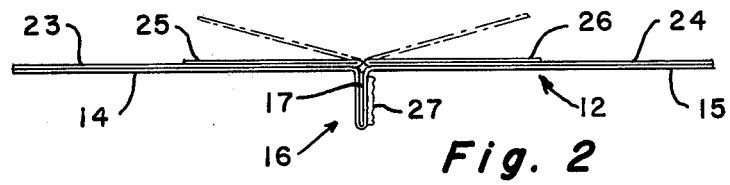
FIG. 2 is a top view of the tube holder shown in FIG. 1.

Strip 12 is shown in greater detail in FIG. 2 as comprising first and second elongated adhesive-backed portions 14 and 15, with an interconnecting portion 16, formed by doubling the strip over itself. Portion 16 receives one end 17 of a locking strip 18. The oppositely positioned adhesive-backed surfaces of portion 16 adhere to end 17 and retain it in secure position. At least the major portion of locking strip 18 comprises a material including hook forming threads 19, which is commonly sold under the trademark "Velcro." This is shown in greater detail in FIGS. 3 and 4.

Figure 5:
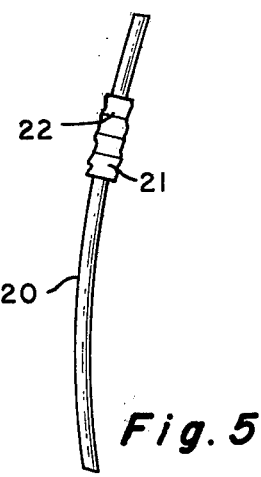
FIG. 5 is an isometric view of a tube with presealed ring portion according to the invention.

The endotracheal tube used in conjunction with the tube holder of the invention is shown in detail in FIG. 5 of the drawings. Tube 20 is selected depending upon the particular patient. Thus, the diameter of the tube and its length, and the set position of presealed ring 21 thereon is determined by normative charts which are regularly used by those skilled in the art. Presealed ring 21 has a plurality of marked positions 22 whereby the length of insertion of the tube into the patient can be varied and determined. The presealed ring 21 comprises a cloth or other fluffy material, which readily engages with the "Velcro" material of the locking strip 18 to form a lock therewith. It is also a soft material, in order that it will not lacerate the lips and bucal mucosa should it come in contact therewith, and is non-reactive with fluids which it may normally contact.

The adhesive backed portions 14 and 15 of the support strip which are applied to the face of the patient are shown in detail in FIG. 2 of the drawings. Before use, the adhesive is protected by protective strips 23 and 24, respectively. Each of the protective strips 23 and 24 is bent around itself to form end portions 25 and 26, respectively, as shown by the solid-line illustration thereof in FIG. 2. When it is desired to apply the support strip 12 to the face of the patient, the end portions 25 and 26 of protective strips 23 and 24 are pulled away from their bent positions, as shown by the broken-line representation thereof in FIG. 2, and the protective strips are then stripped away to expose the adhesive surfaces of elongated portions 14 and 15. This is comparable to the normal operation of the product commonly sold under the "Band-Aid" trademark. The support strip 12 is then applied to the face of the patient, as shown in FIG. 1, being centered in the naso-lip area between the lower part of the nose and the upper lip and spreading from cheek to cheek.

Figure 3:
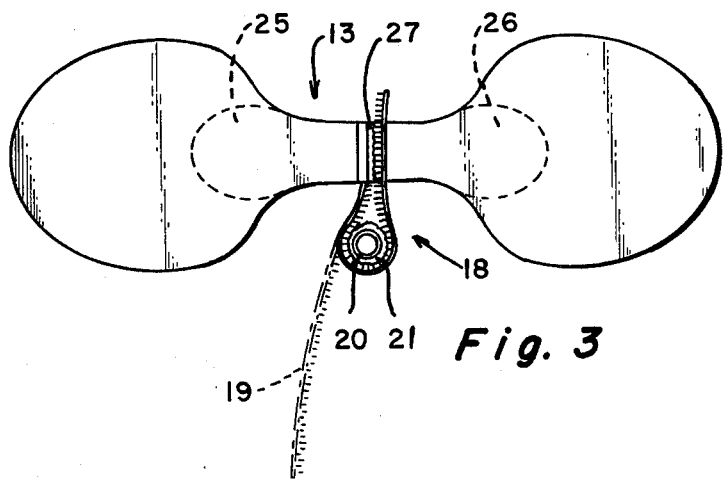
FIG. 3 is a frontal view of the tube holder shown in FIG. 1 with details of the locking strip shown in locked position.
Figure 4:
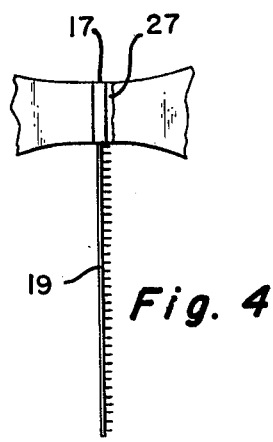
FIG. 4 is a partial front view of the tube holder shown in FIG. 1, with details of the locking strip shown in unlocked position.

The particular endotracheal tube is selected depending upon the size of the patient and the depth of intubation desired. After intubation is accomplished, the "Velcro" portion 19 of locking strip 18 is wrapped around the ring 21. This is shown in detail in FIGS. 1 and 3 of the drawings. In FIG. 3, the broken-line representation of "Velcro" portion 19 illustrates it before it is wrapped around the ring 21. The locked position of "Velcro" portion 19 is shown by the solid-line representation thereof, wherein it is wrapped around ring 21 of tube 20, and then locked to a pad 27 comprising cloth or other fluffy material, which is attached to portion 16, as shown in FIGS. 2 through 4.

The tube is thus solidly fixed in position and accidental slippage and rotation of the tube is prevented. Efficient and rapid adjustment of the tube is possible by varying the locking position of the locking strip with respect to the presealed ring. The relative ease of adjustment, if required, minimizes additional skin trauma to the patient.

The support strip of the invention is configured such that it minimizes the area of the patient's face over which it is applied, but provides maximum support and securement for the endotracheal tube, thereby minimizing patient discomfort. Its configuration permits movement of the patient's mouth, and minimizes the possibility that fluids might seep thereunder, which could cause sores, infections, and the like.

It will be apparent to those skilled in the art that various modifications and variations could be made in the tube holder of the invention without departing from the scope or spirit of the invention.

What is claimed is:

1. An assembly of an endotracheal tube and an endotracheal tube holder for securing the endotracheal tube in a selected position in a patient's trachea comprising:
   a support strip having an adhesive-backed material to secure the support strip to the patient's face, the support strip being configured to be positioned only in the naso-lip area of the patient's face between the lower portion of the nose and the upper lip and to spread from cheek to cheek;
   a locking strip comprising a "Velcro" material portion;
   a pad comprising a material which interlocks with "Velcro" material;
   the support strip defining an integral interconnecting portion to which the locking strip and the pad are attached;
   the endotracheal tube having a presealed ring at a selected location comprising a material which interlocks with "Velcro" material, whereby the locking strip can be locked around the presealed ring and to the pad to lock the tube in the selected position and prevent rotation thereof, the presealed ring being marked to define different levels of intubation.

2. The endotracheal tube holder as recited in claim 1 wherein a protective strip is applied to the adhesive-backed material when it is not in use, the protective strip having end portions for easy removal of the protective strip from the adhesive-backed material.

3. The endotracheal tube as recited in claim 1 wherein the interconnecting portion extends outwardly from the parts of the support strip applied to the patient's face.

* * * * *